United States Patent [19]
Anbar

[11] Patent Number: 5,810,010
[45] Date of Patent: Sep. 22, 1998

[54] DETECTION OF CANCEROUS LESIONS BY THEIR EFFECT ON THE PERIODIC MODULATION OF PERFUSION IN THE SURROUNDING TISSUES

[76] Inventor: Michael Anbar, 145 Deer Run Rd., Amherst, N.Y. 14221

[21] Appl. No.: 368,161

[22] Filed: Jan. 3, 1995

[51] Int. Cl.⁶ .................................................. A61B 6/00
[52] U.S. Cl. .................. 128/664; 128/653.1; 128/691; 128/661.08; 128/653.3; 128/632
[58] Field of Search .............................. 128/661.08, 691, 128/737, 736, 653.1, 664, 665, 742, 65.3, 637, 632, 633, 653.2

[56] References Cited

U.S. PATENT DOCUMENTS

| | | | |
|---|---|---|---|
| 4,809,701 | 3/1989 | Le Bihan et al. | 128/653.2 |
| 5,205,293 | 4/1993 | Ito et al. | 128/691 |
| 5,207,222 | 5/1993 | Koizumi et al. | 128/653.2 |
| 5,207,227 | 5/1993 | Powers | 128/691 |
| 5,233,994 | 8/1993 | Shmulewitz | 128/661.08 |
| 5,445,157 | 8/1995 | Adachi et al. | 128/664 |
| 5,588,437 | 12/1996 | Byrne et al. | 128/664 |

*Primary Examiner*—Brian L. Casler
*Attorney, Agent, or Firm*—Thomas J. Colson, Esq.

[57] ABSTRACT

The present invention comprises methods and apparatus for cancer detection involving the measurement of temporal periodic changes in blood perfusion associated with immune response, occurring in neoplastic lesions and their surrounding tissues. Particularly, the method for cancer detection involves the detection of non-neuronal thermoregulation of blood perfusion, aberrant modulation of blood perfusion, aberrant temperature oscillations associated with blood perfusion, aberrant thermoregulatory frequencies associated with blood perfusion, and periodic changes in the spatial homogeneity of skin temperature.

14 Claims, 4 Drawing Sheets

DETECTION OF CANCEROUS LESIONS BY THEIR EFFECT ON THE PERIODIC MODULATION OF PERFUSION IN THE SURROUNDING TISSUES

TECHNICAL FIELD

The present invention relates generally to cancer detection involving the measurement of temporal periodic changes in perfusion, associated with immune response, that occur in neoplastic lesions and their surrounding tissues. While this has applications to cancer detection throughout the human body, it is practically applicable to a breast cancer screening test involving the measurement of temporal changes in perfusion over large areas of the breasts to identify a localized immune response. Generally, a full work-up, such as ultrasonic scan, needle or incision biopsy, or stereotactic biopsy based on detailed mammographic image, is preceded by a positive finding on a breast cancer screening test. The present invention has many significant differences and advantages over breast cancer screening tests known in the art, as well as general cancer detection methods.

BACKGROUND OF THE INVENTION

I. Prior Art and Competing Technologies

Cancerous lesions have been generally located by their space occupying properties detectable by palpation or by imaging techniques, such as X-ray radiography, X-ray computerized tomography (CT), ultrasonic imaging, or magnetic resonance imaging (MRI). In certain cases, such as breast cancer, detection of cancer is made possible by the enhanced blood supply (hyperperfusion) associated with the neoplastic lesion. In shallow lesions, such as breast cancer, this hyperperfusion results in local hyperthermia.

Hyperthermia of cancerous breasts has been used to detect breast cancer. In classical thermal imaging (thermography) the skin temperatures of both breasts is measured either by liquid crystal contact thermography (LCCT) or by infrared imaging. The bulk temperatures of both breasts is also measured by microwave telethermometry. The difference between the temperatures of the cancerous breast and the non-cancerous breast is often not identified as a signal for further cancer testing since the temperature difference is very similar to differences between two non-cancerous breasts. Temperature differences may occur for a number of reasons unrelated to the presence of cancer. Therefore, the sensitivity and specificity of breast cancer detection by such measurements of temperature are too low to make them useful as a practical screening test. The present invention does not use differences between the temperatures of the two breasts as; a diagnostic criterion.

X-ray mammography (XRM) is a widely used technique for breast cancer screening prior to full diagnostic work-ups. It uses the higher density of calcium minerals and the higher absorbance of X-rays in calcium atoms due to the photoelectric effect, to detect microcrystals of calcium minerals, generally calcium phosphates, that deposit interstitially in cancerous tissue. The characteristic shadow of the relatively opaque microcrystals of calcium minerals on the radiograms, indicates their presence in tissue. A draw-back of XRM as a breast cancer screening test is the occurrence of microcalcification or calcification in benign lesions, hence only a fraction of breasts that manifest microcalcification contain malignant tissue. False positive XRM results are common, and lead to full diagnostic work-ups which often times prove to be negative for breast cancer. The present invention does riot use calcification or microcalcification of tissue as a diagnostic criterion.

Since pathological microcalcification occurs subsequent to tumor formation, it occurs later than the immune response to neoplastic cells, which invokes macrophage activity and enhanced nitric oxide production. Therefore, breast cancer detection by XRM occurs later than detection by the present invention.

Furthermore, the present invention is significantly less expensive than XRM. The equipment needed for the present invention costs less than one third of the cost of XRM equipment. The facility required for the present invention is substantially less expensive (radiation shielding is required with XRM), the personnel needed for the present invention procedure requires substantially less training and is not exposed to any professional hazard (ionizing radiation). Moreover, the present invention does not require and expert's image recognition, whereas XRM requires the expertise of a radiologist. Consequently, the actual cost of the present invention is significantly lower than the cost of XRM. A benefit/cost analysis shows that even if the sensitivity and specificity of the present invention test simply match those of XRM, the present invention is more beneficial, even on purely economic grounds.

Additionally, the present invention poses zero risk to the patient. On the contrary, even with the use of modern mammographic equipment there is a finite risk of cancer induction by XRM. The risk is at least I in 100,000, and more likely substantially larger.

About 500 women, therefore, will contract breast cancer per year if mammography is routinely used by the entire population. Additionally, the present invention causes much less discomfort to the patient than the squeezing of the breasts that must be done in adequate mammography.

The current sensitivity and specificity of XRM are far from satisfactory, especially in flat and in dense breasts. The present invention is substantially more sensitive and specific than classical thermal imaging, (which was shown to be only slightly less effective than XRM) and, therefore, is superior to XRM in diagnostic efficiency.

Since the present invention measures the immune response, while XRM must wait for microcalcification of the tumor to make it detectable, the present invention can detect breast cancer substantially earlier than XRM. Since the outcome of treatment of breast cancer is more favorable the earlier cancer is detected, the present invention has a substantial advantage over XRM in improving public heath.

II. Dynamic Area Telethermometry

Dynamic Area Telethermometry (DAT) is a known concept and described fully in 1991 publication of Dr. Michael Anbar, *Thermology* 3(4):234–241, 1991. There is, however, no known practical application for DAT in the public domain. It is a non-invasive, functional test of the autonomic nervous system, that monitors changes in the spectral structure and spatial distribution of thermoregulatory frequencies (TRF's) over different areas of the human skin. Grounded in the science of blackbody infrared radiation as measured by infrared imaging, DAT derives information on the dynamics of heat generation, transport, and dissipation from changes in the temperature distribution over areas of interest. Changes can be detected in the average temperatures of area segments or in the variances of those averages; the variances measure the homogeneity of the temperature distribution and, therefore, the homogeneity of cutaneous perfusion (under conditions of hyperperfusion the homogeneity reaches a maximum and the amplitude of its temporal modulation is at a minimum). From the periodic changes in temperature distribution over different skin areas, the thermoregulatory frequencies of the processes that control the temperature in the given areas can be derived.

From the periodic changes in the spatial homogeneity of skin temperature (HST), the processes that control the saturation of the cutaneous capillary bed can be derived. HST is the reciprocal of the spatial coefficient of variation of temperature in small ("micro") areas of skin (<100 mm$^2$): HST=average temperature divided by the standard deviation of the average temperature (HST is a dimensionless parameter). HST is determined by the structure of cutaneous vasculature and by its heat dissipatory activity. As perfusion is enhanced, more capillaries are recruited as blood conduits and HST increases. Unlike average temperature, HST is affected mainly by the behavior of the cutaneous capillaries and to a much lesser extent by the blood flow in subcutaneous vessels. The neuronal control of HST is, therefore, different from that of skin temperature. Consequently, HST is an independent physiological hemodynamic parameter. Like the average temperature of unit areas of skin, HST oscillates as a function of the temporal behavior of perfusion. Since the rate of increase of HST with the extent of perfusion is much higher than that of temperature, the extent of its change and the amplitude of its modulation are significantly higher than those of temperature change and temperature modulation. A static image of HST is, therefore, more informative than a classical thermogram. The concept of HST has been fully described by Dr. Michael Anbar in *Advanced Techniques and Clinical Applications in Biomedical Thermology*, Mabuchi K., Mizushina S. and Harrison B. (Eds.) Harwood Academic Publishers, Chur, Switzerland, 1994 (published January 1995), pp. 173–187.

Quantitative DAT requires high-precision measurement of infrared flux (corresponding to <0.01° C.), low electronic and instrumental noise(<0.0005° C. equivalent of electronic or thermal noise), and long-term stability (drift of <0.1° C./hr). All these are attainable with current commercial equipment. The minimal resolution required for DAT is an image field of 128×128 pixels, which can be optically zoomed to cover an area of 10 to 10000 cm$^2$ (0.06 mm$^2$ to 0.6 cm$^2$/pixel). To guarantee correct recognition and precise location of the anatomic features studied, it is beneficial to simultaneously generate a reflective image of exactly the same body area (to precisely record the anatomic features), and superimposie the reflective over the emissive image to assure precise registration of any thermal abnormalities found. This concept has been fully described in a 1993 publication of Dr. Michael Anbar, SPIE Proceedings 2020: 510–517, 1993.

DAT is useful in the diagnosis and management of a large variety of disorders that affect neurological or vascular function. DAT is used to measure the periodicity of changes in blood perfusion over large regions of skin so as to identify locally enhanced immune response, thereby providing a quick, inexpensive screening test for skin cancer and for relatively shallow neoplastic lesions, such as breast cancer. The different clinical applications of DAT are fully described by Dr. Michael Anbar in 1994 in a monograph entitled "Quantitative and Dynamic Telethermometry in Medical Diagnosis and Management", CRC Press Inc. September, 1994.

The substantially lower cost of infrared equipment, and the substantially lower personal training requirements, make DAT tests substantially less costly than radiological, ultrasonic, or Nuclear Magnetic Resonance (NMR) based computerized imaging tests, such as CT (computerized tomography), SPECT (single photon emission computerized tomography), PET (positron emission tomography), or MRI (magnetic resonance imaging). Being utterly non-invasive, DAT tests are risk free and cause significantly less discomfort to the patient than some of the neuromotor tests, such as EMG, or nerve conduction tests. They also take less time than other scanning tests (CT, MRI, or ultrasonic tests, respectively).

III. Measurements

A. Thermoregulation.

Skin, the largest organ of the human body, plays a major role in regulating the body's core temperature. In its heat dissipatory role, skin generally becomes warm when the body needs to dissipate excessive heat, and turns cold when the body must preserve heat. Under moderate environmental conditions, skin temperature depends primarily upon the blood flow in the vasculature below the skin surface.

Skin temperature reflects the physiological behavior of cutaneous blood flow which is modulated by the neurological control of pertinent arteries and arterioles.

Observing skin temperature at any point on the skin as a function of time can provide direct information on the neurological control of arterial circulation. Neurological disorders can, therefore, be associated with abnormal temporal behavior of skin temperature, in addition to changes in spatial distribution of thermoregulatory function, both of which lend themselves to quantitative assessment. Like in other neurological or neuromuscular tests, substantial diagnostic information is embedded in the dynamic behavior of the thermoregulatory system.

Although skin temperature may vary over a wide range, depending upon the environment and on the level of metabolic activity, it is regulated under normal conditions. This regulation may be occasionally less stringent, like during sleep; but even then, some skin regulation is retained. Like any regulated parameter, including core temperature, skin temperature is expected to oscillate around a set point, even if the value of the set point does not remain constant. Even a simple thermostated system, such as a forced air heated and cooled house, will show temperature oscillations stemming from temperature over-shooting and delays due to imperfect thermostats and different rates of response and relaxation of the individual heating and cooling processes. In the human body, skin temperature maintenance is due, in substantial part to neuronal thermoregulation of vasoconstriction and vasodilation of the vasculature, thereby causing a characteristic modulation of blood perfusion. That is, unless the neuronal thermoregulation is inhibited or taken over by a non-neuronal thermoregulatory control, such as Nitric Oxide (NO). In a complex regulated system, such as the human body, where there are several levels of non-linear regulatory processes interacting with each other, many thermal regulatory oscillations are superimposed on each other. To deconvolute these into systemic, regional, and local thermal regulatory processes, one has to probe different parts of the body, and different regions of organs.

In order to maintain or change skin temperature, the neuronal thermoregulatory system constricts or dilates its blood vessels to change the rate of blood flow in the vessels. As indicated above, this is not the case if the neuronal thermoregulation is inhibited in certain regions by an independently functioning agent, such as (NO). That region is then under no-neuronal thermoregulatory control.

NO has been recognized as a ubiquitous vasodilatory chemical messenger. Its main role appears to be synchronization of intercellular and intracellular functions, as it diffuses freely in the interstitial space. It can, therefore, inhibit sympathetic vasoconstrictive control in substantial regions of the microvasculature and cause regional hyperperfusion. Subcutaneous and cutaneous hyperperfusion are manifested as hyperthermia of the overlying skin. Augmented immune response, such as encountered in local infections, autoimmune diseases, and cancer, is associated with enhanced NO production. Under certain conditions, such as in breast cancer, autocatalytic production of NO may occur, which results in oscillatory vasodilation, independent of and substantially different from the temperature oscillations of perfusion caused by the neuronal thermoregulatory system.

B. Mechanism of Local Hyperthermia of Cancerous Breasts.

Cancer associated breast hyperthermia is caused by impaired neuronal thermoregulation. This impaired neuronal control is caused by excessive production of NO by macrophages that react to the neoplastic tissue. This macrophage activity is an expression of the immune response, because NO generated by macrophages is a major factor in killing of microorganisms or of mammalian cells recognized as alien.

This mechanism is described fully in a 1994 publication of Dr. Michael Anbar, *Cancer Letters* 84(1):23–29, Sept. 15, 1994. The macrophage generated NO, that diffuses freely throughout the surrounding tissues, interacts with the vasoconstrictive receptors in the arterioles so as to vasodilate the vasculature. This results in enhanced perfusion of the capillary bed. As a consequence of the characteristic multiphasic synergistic action of NO, this augmented perfusion enhances migration of additional macrophages to the site of the tumor. The rate of production of NO is further enhanced by the presence of ferritin, the level of which is significantly elevated in breast cancerous tissue. $Fe^{2+}$ released from ferritin is used to produce more NO synthase (NOS), an iron carrying enzyme which produces NO from argiline, and thus results in a further increase in the rate of production of NO. $Fe^{2+}$ also catalyses the formation of free radicals needed in the synthesis of NO.

Furthermore, NO has been shown to release $Fe^{2+}$ from ferritin, by forming an NO-ferritin complex. This results in an autocatalytic production of NO. $Fe^{2+}$ also reacts with nitrite, the oxidation product of NO, to reform NO. This maintains the local high level of NO, and the hypoperfusion of the capillary bed. The ferritin dependent enhancement of NO production seems to be specific to neoplastic cells and is less likely to occur in other inflammatory situations, including those induced by microorganisms.

NO diffuses readily interstitially; therefore, the volume of the capillary bed that is hyperperfused is many-fold larger than that of the tumor and its immediate surroundings. This explains the extensive regional hyperthermia associated with minuscule antigenic tumors. The rate of NO production in the cancerous breast is also amplified by the positive effect of the local temperature on NO production by the macrophages. All those autocatalytic effects overshadow the negative feedback of NO level on the rate of enzymatic NO production.

Like any autocatalytic process, the rate of NO production is expected to oscillate.

The rate of NO production is expected to rise exponentially due to the positive feedback of $Fe^{2+}$ and of temperature, and then fall when certain precursors, such as, arginine or oxygen, are temporarily locally depleted. A similar positive feedback, resulting in vascular oscillations, has been demonstrated for NO under ischemic conditions in the brain, where the lack of oxygen results in lower production of NO and a subsequent vasoconstriction, which further limits oxygen supply.

The macrophage enhanced generation of NO and its extensive perfusion throughout the capillary bed inhibit, or even take complete control of the modulation of blood perfusion from the neuronal thermoregulatory system and, therefore, overshadow the neuronal thermoregulatory temperature oscillations. Since the extent of perfusion and the surface temperature of the overlying skin follow the same oscillatory behavior, the temporal behavior skin temperature over the macrophage infiltrated region does not follow the normal neuronal thermoregulatory modulation in blood perfusion. The infiltrated region, therefore, does not maintain normal temperature oscillations or thermoregulatory frequencies resulting therefrom.

The frequencies of temperature oscillations observed over the cancerous breast differ substantially from those observed over the non-cancerous (normal) breast. The oscillations over the normal breast are caused by the neuronal thermoregulatory processes, which follow several characteristic bands of frequencies. The cancerous area of the breast, on the other hand, which loses its neuronal thermoregulatory control due to the over-production of NO, is characterized by the disappearance of the neuronal oscillations and the appearance of oscillations due to the autocatalysis of NO production, with their typical frequency bands. Since the latter autocatalytic processes, which are controlled by the temporary local depletion of one of the precursors of NO, are utterly different in nature from the neurological feedback processes manifested in the neuronal frequency bands, there is no possibility of frequency overlap of these entirely different processes over all frequency bands. The disappearance of the neuronal frequencies over substantial parts of the cancerous breast is sufficient to identify pathology. Furthermore, the appearance of the autocatalytic frequencies characteristic of NO over-production is, by itself, sufficient to identify pathology. The substitution of one set of frequency bands by the other is an even more strict criterion of pathology.

Under conditions of NO overproduction and its consequent hyperperfusion, HST reaches a maximum value that oscillates at a frequency that depends on the modulated autocatalytic rate of NO production. The frequency bands of the modulation of HST can be used, therefore, as independent criteria of pathology. The combination of the temperature and HST TRF criteria increase the sensitivity and specificity of the DAT test.

Since, unlike classical thermography of the breast, the DAT test does not use the absolute temperature or temperature differences as a diagnostic parameter, there is less need to allow the patients to reach thermal equilibrium with the environment. This means faster turnover of patients, hence lower cost per test. Moreover, the environment does not have to be strictly controlled, as long as it does not contain modulated infrared emissions in the frequency ranges of interest, that might be reflected from the skin. This lowers the cost of the installation. Since the overwhelming majority of screened subjects are free of malignancy, the administration of the test can be fully computerized and does not require medical expertise. The extensive computerization which allows the use of easily trained semi-skilled personnel, provides a substantially lower cost of this screening test, as compared with the prior art (including the classical thermological tests).

C. Alternative methods to measure periodic changes in perfusion.

As stated, DAT is the method of choice to measure modulation in blood perfusion. Microwave thermometry of the bulk tissue and thermometry of the skin using arrays of thermistors, are two alternative methods to dynamically measure temperature. Microwave thermometry has, however, a significantly lower spatial resolution (by a factor of 10,000) and lower sensitivity (by a factor of 10 to 100), and it may require direct contact of the electrodes (antennas) with the breast, which calls for skill and additional time. Area thermometry by thermistors with adequate spatial resolution requires the mounting of many hundreds or even thousands of thermistors all over the breasts, which is a prohibitively cumbersome process. Liquid crystal contact thermography (LCCT) has too low precision (>0.5° C.) and too long response time to be useful in quantitative dynamic measurements.

Other methods of continuously measuring the modulation of perfusion of the capillary bed in the breast include ultrasound (measuring changes in ultrasonic impedance, because the speed of sound is temperature dependent and because of changes in the average density of hyperperfused tissue, or by measuring changes in the average velocity of erythrocytes by Doppler shift). Ultrasonic measurement of perfusion cannot be done simultaneously on all areas of one or both breasts. It also requires a highly skilled technician to measure the changes in perfusion in different areas. Further, it is necessary to apply a coupling lotion in order to make contact with the ultrasonic probe and the breast. The application of such coupling lotion and the contact of the ultrasonic probe may alter the perfusion by affecting the thermal and tactile neuronal sensors.

Another method of measuring modulation in blood perfusion is infrared Doppler velocimetry (IRDV), which measures the Doppler shift of the near infrared radiation (about 1 $\mu$m) reflected from erythrocytes. IRDV, however, cannot monitor modulation of blood perfusion over large areas in a reasonable time (it would take many hours to accumulate the same information on the temporal behavior of blood perfusion that can be measured in less than 5 minutes by DAT).

Another method to measure modulation in blood perfusion is single photon emission computerized tomography (SPECT), which measures the local concentration of radioactively labeled compounds in tissues inside the human body. Red blood cells can be labeled by a radioactive isotope and their concentration in a tissue of interest is a measure of perfusion. SPECT, however, does not measure concentrations with a precision that allows to monitor small (say, 1%) modulations of perfusion. Moreover, SPECT entails radiobiological risk to the patient, is more cumbersome and time consuming, and involves much more expensive instrumentation compared with DAT.

Another method of measuring modulation in blood perfusion is impedance plethysmography (because the ionic conductivity depends on the amount of plasma between the electrodes). This method, which requires the mounting of an array of electrodes on the two breasts by a skilled technician before any measurement can be done (which makes it substantially more expensive), is also less sensitive to minute oscillations; further, its spatial resolution (limited by the number of electrodes used) is significantly lower than achieved by DAT.

Yet another method of continuously measuring the modulation in perfusion of the capillary bed in the breast is MRI. MRI can be used to dynamically monitor blood perfusion and detect characteristic oscillations associated with the autocatalytic NO controlled mechanism. However, MRI requires much more expensive instrumentation than DAT (by a factor of 30 to 60), and an examination would be much more cumbersome and time consuming. MRI, more importantly, can be used to identify deeply situated cancerous lesions, that do not effect cutaneous or subcutaneous perfusion, and are, therefore, not amenable to DAT tests.

Since the modulation of blood perfusion of the cancerous breast is directly related to the modulation of NO in the affected tissue, measuring the concentration of NO and its modulation could be used as an alternative diagnostic method for cancer detection. The most preferred method of measuring the concentration of NO in human tissues is by electron paramagnetic resonance (EPR) operating in an imaging mode. Imaging EPR is conceptually very similar to MRI (it uses different electromagnetic frequencies). The cost of an EPR imaging test will, therefore, be comparable with an MRI test. Like MRI, EPR imaging can be used to identify deeply situated cancerous lesions, that do not affect cutaneous or subcutaneous perfusion, and are, therefore, not amenable to DAT tests.

BRIEF DESCRIPTION OF THE DRAWINGS

The invention will become more readily apparent from the following description of preferred embodiments thereof shown in the accompanying drawings, wherein.

DETAILED DESCRIPTION OF THE PREFERRED EMBODIMENTS.

Figure 1:
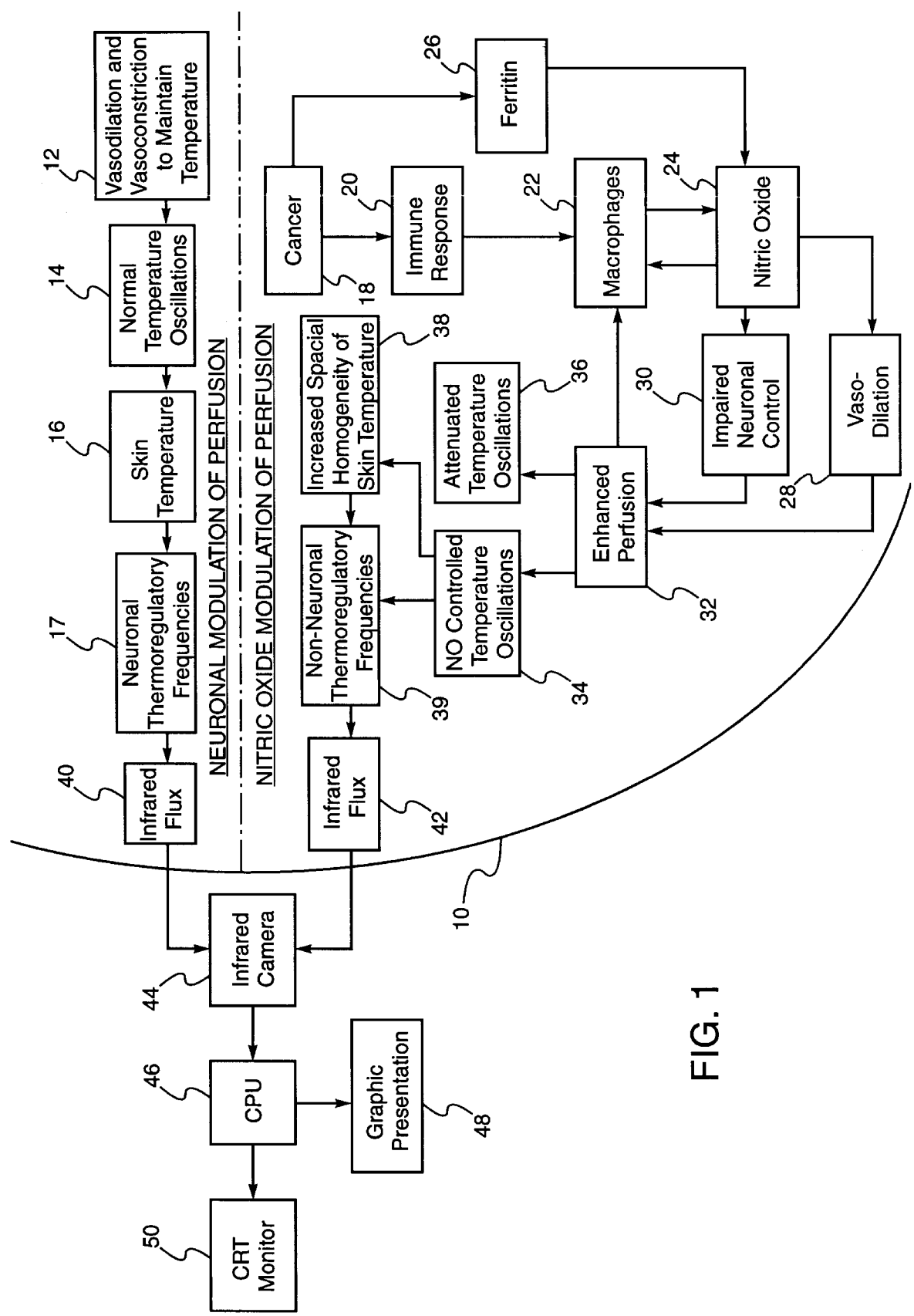
FIG. 1 is a graphic representation of the invention in black box form showing each of the components and steps thereof.

As shown in FIG. 1, a non-cancerous region of the breast maintains a required temperature by neuronal modulation of blood perfusion 12. Furthermore, this modulation of blood perfusion generates temperature oscillations 14, from which normal neuronal thermoregulatory frequencies 17 can be derived.

As further shown in FIG. 1, a cancerous region of the breast provokes immune response 20 which enhances the activity of macrophages 22 that produce NO 24. This NO production is enhanced by the elevated level of ferritin 26 in the breast cancerous tissue. Moreover, as further shown in FIG. 1, the presence of NO vasodilates the vasculature 28 causing enhanced perfusion of the capillary bed 32. The presence of NO impairs neuronal control of vasoconstriction and vasodilation of the vasculature 30, thereby changing the modulation of perfusion and the temperature oscillations 34, 36 manifested therefrom. As shown further in FIG. 1, aberrant modulation of perfusion increases the HST 38 and causes attenuated or non measurable neuronal thermoregulatory frequencies 39; hence, an aberrant infrared flux. As described above, each of these are measurable phenomena.

The screening technique uses the characteristic changes in the temporal behavior of blood perfusion caused by enhanced NO production by macrophages 22 and amplified by ferritin 26 to detect immune response 20 induced by neoplastic disease. The temperature oscillation of blood perfusion associated with the autocatalytic production of NO, as well as the diminution or disappearance of the neuronal TRFs are used as the diagnostic parameters. Like skin temperature, HST changes from neuronal to NO controlled modulation. The TRFs of HST are, therefore, additional independent diagnostic parameters.

The neuronal and autocatalytic oscillations are measured by fast Fourier transform (FFT) analysis, an analysis method well known in the art, of the temporal behavior of breast perfusion (manifested in the temporal behavior of breast temperature and of HST). As discussed above, modulation of perfusion of the capillary bed in the breast can be continuously measured by several techniques. Because of its sensitivity, fast response time, speed of data acquisition and low cost, DAT is the preferred method of measuring modulation of perfusion of the capillary bed and identifying aberrations in parts of human tissue. It possesses a sensitivity of up to 0.001 ° C. (i.e., about 50 times smaller than the level of temperature modulation under conditions of normal perfusion; the autocatalytic process is expected to have an even higher level of modulation) and a response time of <10 msec. The TRFs of HST are derived from the same DAT data, using the same computational technique, only that in this case the measured parameter used in the Calculation is the spatial "micro" variance of temperature.

Figure 2:
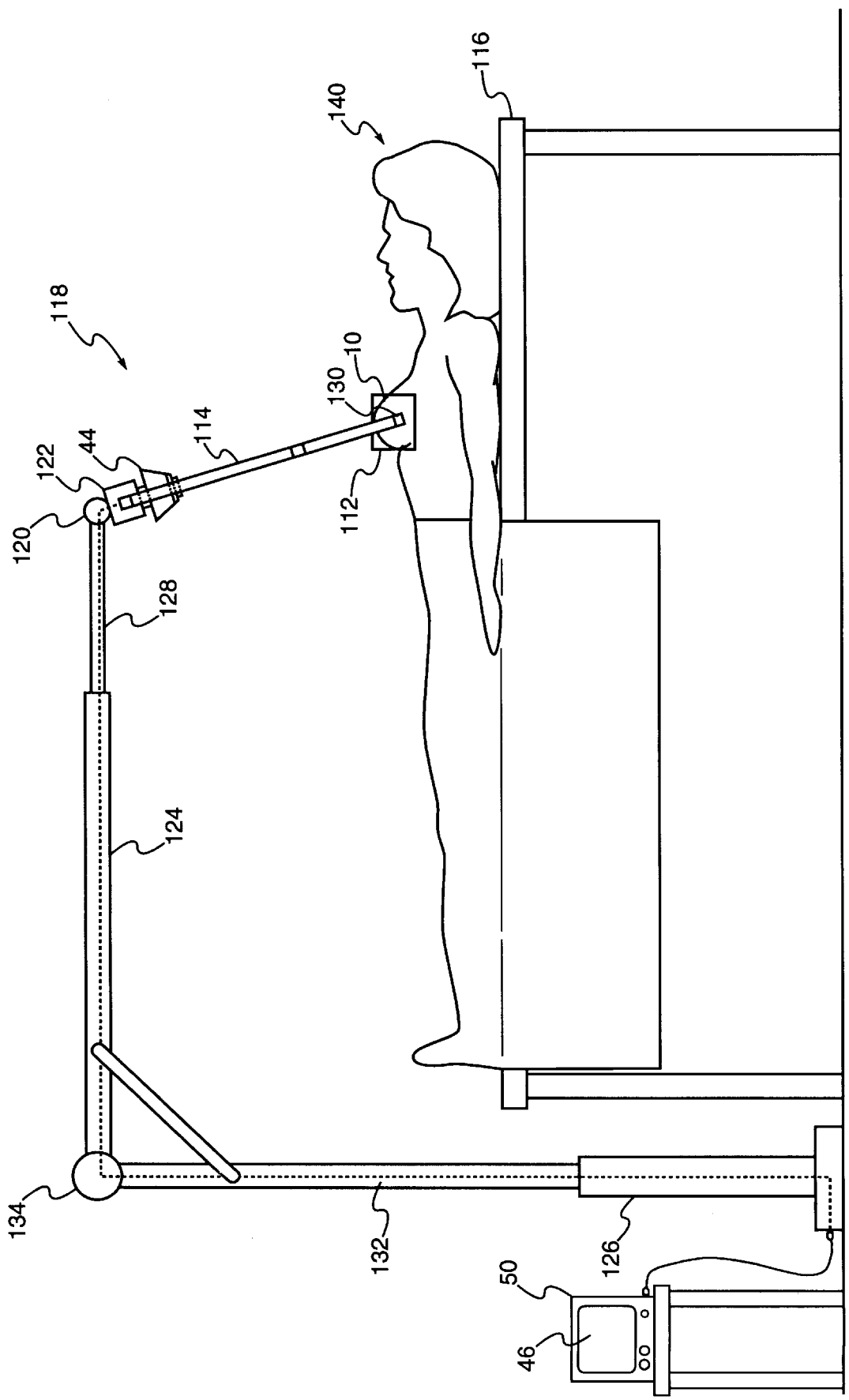
FIG. 2 is a side elevational view of the preferred embodiment of the apparatus of the invention.

As shown in FIG. 2, DAT facilitates the simultaneous monitoring of the complete areas of both breasts including their lateral views by using mirrors. Such simultaneous monitoring over time of complete areas of both breasts is the preferred method. It allows for the accumulation of hundreds of sequential thermal images that are then subjected to FFT to extract the frequencies and amplitudes of periodic changes at each pixel of the image. To measure the HST, the image is subdivided into a matrix of small areas, each corresponding to 64 mm$^2$ of skin, and the temperature values of the pixels in each subarea of the image are averaged. The variance of the average temperature is used to calculate the HST of each subarea. The HST values of all the accumulated images are then analyzed by FFT to extract the corresponding TRFs.

DAT requires a highly stable, high resolution, highly sensitive, computerized infrared camera, preferably operating in the 8 to 14 $\mu$m range. To meet the specific DAT needs it is preferred that the camera's computer be programmed to quantitatively analyze the temporal behavior of many thermal images with a sufficient resolution (e.g., 256×256 pixels; the geometry of the image of both breasts with the reflected images of the lateral views optimally requires a field of view of 256×512 pixels). While successful results can be achieved by analyzing the temporal behavior of at least 64 thermal images, it is most preferred to measure 512 thermal images. These images are temporarily stored using an appropriate compression scheme, because one needs the data of all the images to perform the FFT on the time series of temperature values of each pixel or subarea. The FFT yields the frequency spectra of each pixel together with the relative amplitude of each TRF. The software then tabulates or displays the spatial distribution of the TRF's within a given range of relative amplitudes over the image. The same procedure is followed with the HST data.

When TRF's are displayed with amplitudes above a given threshold (e.g., above 5% of the total thermal modulation, or a certain cut-off value in the rank order of amplitudes) a subset of characteristic neuronal frequencies over areas of breasts free from cancer-enhanced immune response is identified; these TRF's are significantly attenuated or completely absent in areas overlying breasts with neoplastic lesions. The latter areas are characterized by substantially different TRF's caused by the autocatalytic production of NO and exhibit, therefore, the non-neuronal thermoregulatory behavior. Also the latter areas are, therefore, characterized by aberrant modulation of blood perfusion and aberrant temperature oscillations. A hard copy image is then generated to allow an expert to anatomically identify the location of the aberrant area, or areas. The infrared camera can be equipped also with video CCD (or, in a scanning camera, with a photodiode detector), to produce a reflective (visual) image of the patient's breasts. The reflective image allows precise anatomical location of areas with aberrant temporal behavior, information needed for further work up of such a patient.

The computer algorithms that facilitate this computation are as follows

A. Use of temperature values of individual pixels and the computation of TRFs.

1. The computerized camera takes an image of the infrared flux (256×512 pixels) and converts it into a thermal image where each pixel has a certain temperature value. This process is repeated, preferably, twice a second (or 5 times a second, or once a second, or once every 2 seconds) until 512 thermal images have been accumulated and stored.

2. The computer now extracts the temperature value of the same pixel in each of the 512 images, discarding any pixel I-hat has a temperature value below 26° C. (pixels that do not represent human skin, which are excluded from the set of selected pixels). These temperature values constitute a single time series, that is then subjected to FFT analysis to extract the contributing frequencies and their relative amplitudes. The computer stores the FFT spectrum for the given pixel. The computer repeats the same procedure for each of the selected pixels of the image.

3. The computer picks the FFT spectrum of a selected pixel, rank orders the amplitudes, and selects the 10 highest amplitudes in this series. It then stores the frequencies that have those prominent amplitudes. The computer repeats this procedure for each of the selected pixels of the image.

4. The computer picks the highest of all ten most prominent frequencies of a selected pixel and checks all the other selected pixels if they identified that frequency as one of their prominent ones. This frequency is tabulated together with a number (MV=matching value) equal to the number of pixels that contained that frequency among their 10 most prominent ones. This procedure is repeated for each of the 10 prominent frequencies identified. The computer picks then the next pixel and repeats this procedure for all frequencies that were not identified in the first match. This is repeated for half of the selected pixels.

5. The computer then rank orders the MVs and selects the 16 most common frequencies as well as their preceding and following frequencies (FFT produces a series of discrete frequencies) to identify frequency bands. It then calculated the sums of the absolute amplitudes (in ° C.) of the tabulated 16 (or less, since two adjacent frequencies may belong to the 16 most common frequencies) most common frequency bands. It can display at this point the spatial distribution of amplitudes of each of the 16 most common frequencies, by color coding the amplitudes. These displays facilitate visual identification of areas that have exceptionally high or exceptionally low most common frequencies.

6. The computer then averages the amplitudes of all selected pixels that share one of the most common frequencies and identifies all the pixels that have amplitudes higher than say, 30% below average, and stores that list (each pixel is identified by its coordinates). It then tabulates in a second list all the selected pixels that were not included in the first list. Then it checks the 8 next neighbors of each of these pixels to find out if they are in the second list, and thus identifies congruence of low amplitude or zero amplitude pixels. If it identifies a subset of more than say, 100 such congruent pixels (roughly 100 mm$^2$) it declares that array of pixels as aberrant for that given frequency. The computer then repeats the same procedure with each of the 16 most common frequencies.

7. The computer then checks for overlaps of the aberrant areas identified in procedures #5 and #6 and selects as definitely aberrant areas those that were identified by 3 frequency bands or more (demonstrated significant attenuation of neuronal frequencies).

8. If procedure #7 does not identify definitely aberrant areas, the computer prints out a message that the findings are negative and the patient is normal.
Otherwise, the computer proceeds with procedure #9.

9. The computer examines all the pixels in the aberrant areas identified in procedure #7, for their 10 most prominent frequencies (see procedure #4) excluding those that were among the 16 most common frequencies (see procedure #5), and find out, using procedure #4, how many of the pixels inside the aberrant area share 3 or more of those frequencies. If more than 80% of the pixels in the aberrant area share 3 or more most prominent frequencies different from those included in the most common frequencies (see procedure #5), the assignment of the aberrant area is reaffirmed (demonstrated presence of NO modulated frequencies).

10. If procedure #7 identifies a definitely aberrant area, while procedure #9 turns out negative, the computer prints out an image of the breasts in 2 colors, say black and white, with the aberrant area as black. If procedure #9 yield a confirmation, the computer prints out an image with the aberrant areas in white and the rest of the image in black. (This mode of printout allows the use of less expensive monochrome printers).

B. Use of HST values and the computation of HST TRFS.

1. The computer subdivides the image into 2048 square subareas of 64 pixels each (corresponding to approximately 64 mm$^2$ of skin), and calculates the average temperature (AVT) value and standard deviation (SD) of each subarea. The AVT values can be treated identically to the temperature values of individual pixels according to procedures # A1 to A10.

2. The computer then calculates the HS1 value for each subarea: HST=AVT/SD. Time series of HST values are then analyzed by FFT to yield HST TRFs, following procedure #A2.

3. The next steps of the computation follow identical procedures to #A3 to A10, except that in procedure #A5 the absolute amplitude are in HST dimensionless units.

4. Following the last step of procedure #A1 with the HST TRFs, the latter finding, if positive, can be used to confirm the findings of the temperature TRFs. In this case we have 4 independent diagnostic parameters and the printout of the findings must be done with a four color printer (e.g., HP Colorjet, that is still quite inexpensive).

5. The printout of the visual image can be done in halftone monochrome on a transparent mat (e.g., HP 51630Q) that can be overlaid on the aberrant area image, to precisely identify the anatomic position of the aberrant area.

The difference between normal and cancerous breasts is accentuated by a thermal challenge (cooling) of the breasts, which affects only the neuronal thermoregulatory system and therefore affects only TRF's in areas that are not vasodilated by excessive NO production. The computer is programmed to look for the frequency bands of the neuronal and the NO controlled TRF's in every pixel or square subset of pixels (e.g., 25, 36, 49 or 64 pixels) of the FFT processed image. If the computer does not find any pixels with neuronal TRF's having exceptionally low or nil amplitude (except in the periphery of the image which does not depict skin), and no pixels or subareas are found to have the NO controlled autocatalytic TRF's with a significant amplitude, the findings of the test are declared as negative (i.e., normal). This finding is then confirmed by computing and analyzing the HST TRFs. If the computer finds certain pixels with exceptionally low neuronal TRF's and if those pixels exhibit the NO controlled autocatalytic TRF's, the test findings, preferably DAT test findings, will be classified as pathological. This finding is then confirmed by analyzing the HST data, as described for the uncooled breast. Cooling of the breasts (by a mild flow of forced air) attains maximal sensitivity and specificity. Such additional testing are administered as a confirmatory test only to patients who show a positive result on the uncooled test.

As shown further in FIG. 2, in the most preferred embodiment of this invention the apparatus comprises a support means 118 for holding infrared camera 44 in a position to facilitate infrared images from the human body positioned therebeneath. Support means 118 comprises base 126, data cable 132 for transmission of the images from the infrared camera to a CPU 46 and CRT monitor 50. Support means 118 further comprises an arm 124 to extend the infrared camera 44 to a position above the human body, with an extendible portion 128 to allow for movement of the infrared camera horizontally along a human body. Pivot 120 connects infrared camera 44 to the extendible portion 128 of support means 118 and provides for independent movement of infrared camera 44 to obtain images of the human body at angles of a plurality of degrees. Extending downward from arm 124 and specifically from pivot 120 are a second support means 114 for mirrors 112. Mirrors 112 are attached to second support means 114 by a second pivot 130 to enable independent or simultaneous movement of mirrors 112 as needed to provide a side view of breasts 10 for infrared camera 44.

Figure 3:
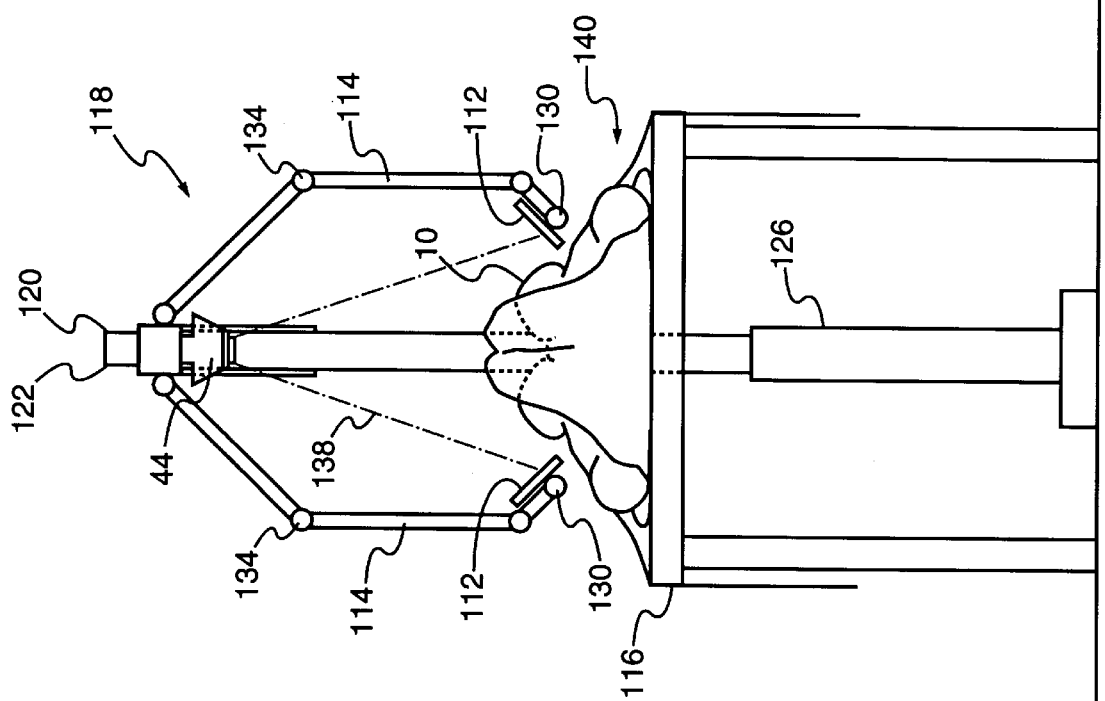
FIG. 3 is a second side elevational view of the preferred embodiment of the apparatus of the invention.
Figure 4:
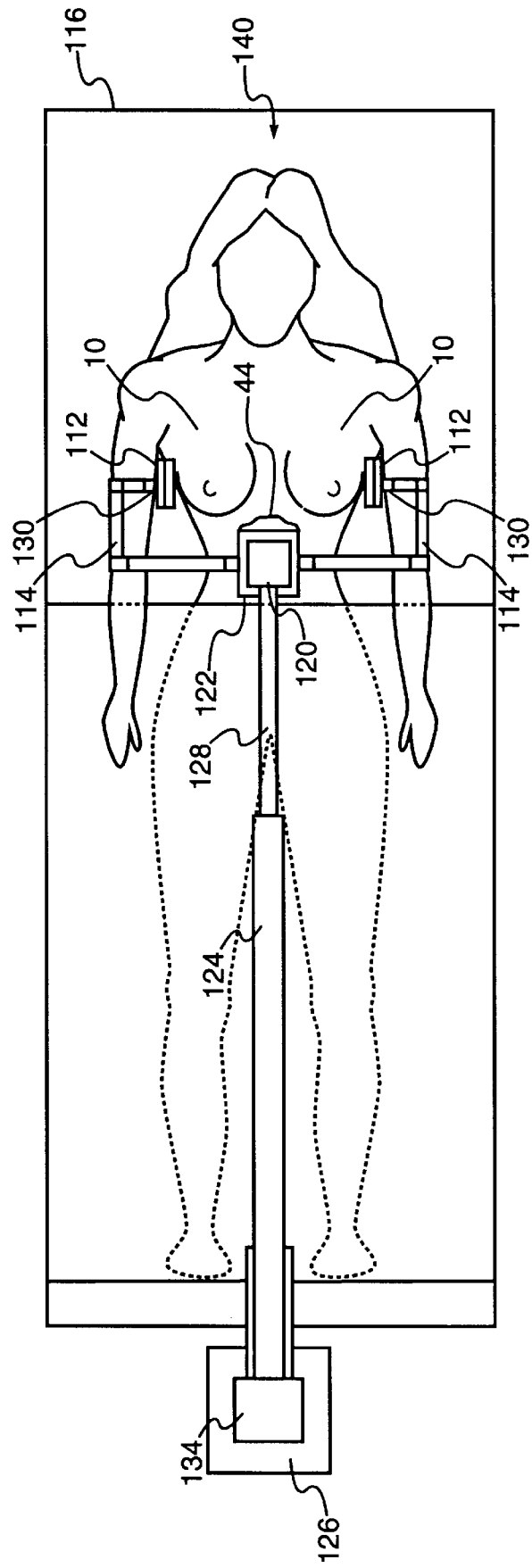
FIG. 4 is a top view of the preferred embodiment of the apparatus of the invention.

As shown in FIG. 3, support means 114 are positioned so as not of obstruct the view of infrared camera 44. This enables infrared camera 44 to obtain complete images of breasts 10. As further shown in FIG. 3, mirrors 112 reflect infrared radiation 138 from side portions of breasts 10 to infrared camera 44. Mirrors 112 are most preferably comprised of aluminum or other infrared radiation reflecting material.

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. A method for detecting cancerous tissue in humans comprising the steps of:
   a) providing a detecting means for detecting changes in a characteristic modulation of blood perfusion in a human organ;
   b) detecting, with said detecting means, said changes in the characteristic modulation of blood perfusion in a human organ; and
   c) identifying as cancerous a region of said human organ wherein said changes in the characteristic modulation of blood perfusion are detected.

2. A method according to claim 1 wherein said detecting means is DAT.

3. A method according to claim 1 wherein said detecting means is an infrared sensing system.

4. A method according to claim 1 wherein said detecting means is MRI.

5. A method according to claim 1 wherein said detecting means is an ultrasound imaging system.

6. A method according to claim 1 wherein said changes in modulation of blood perfusion are manifested by a loss of said modulation of blood perfusion.

7. A method according to claim 1 wherein said detecting means is a Laser Doppler System.

8. A method according to claim 1 wherein said detecting means is a paramagnetic resonance system.

9. A method according to claim 1 wherein said changes in modulation of blood perfusion are detected by the steps of:
   a) providing a means for detecting aberrations in temperature oscillations associated with blood perfusion in a plurality of parts of a human organ;
   b) detecting, with said detecting means, said aberrations in said temperature oscillations in said plurality of parts of a human organ.

10. A method according to claim 1 wherein said changes in modulation of blood perfusion are detected by the steps of:
   a) providing a means for measuring NO concentration in a plurality of parts of a human organ;
   b) providing a means for comparing relative concentrations of NO in said plurality of parts of a human organ;
   c) measuring concentration of NO, with said measuring means, in said plurality of parts of a human organ;
   d) comparing said concentrations of NO in each of said plurality of parts of a human organ;
   e) providing a detecting means for detecting periodic oscillations in the concentration of NO in said plurality of parts of a human organ;
   f) detecting, with said detecting means, said periodic oscillations in the concentration of NO in said plurality of parts of a human organ.

11. A method according to claim 1 wherein said organ is a breast.

12. A method according to claim 11 comprising the additional preliminary steps of:
   a) providing a means for cooling said breast;
   b) cooling said breast to accentuate a variance between a cancerous and noncancerous area of said breast.

13. A method according to claim 1 wherein said organ is skin.

14. A method according to claim 13 comprising the additional preliminary steps of:
   a) providing a means for cooling said skin;
   b) cooling said skin to accentuate a variance between a cancerous and noncancerous area of said skin.

* * * * *